United States Patent
Solano Montenegro et al.

(10) Patent No.: US 12,178,390 B2
(45) Date of Patent: Dec. 31, 2024

(54) STEERABLE ROTATIONAL HEMOSTASIS CLIP

(71) Applicant: BOSTON SCIENTIFIC SCIMED, INC., Maple Grove, MN (US)

(72) Inventors: Esteban Solano Montenegro, Heredia (CR); Diana Catalina Rodriguez Forero, San José (CR); Jairo Mauricio Vargas Mena, Concepcion de San Rafael (CR)

(73) Assignee: Boston Scientific Scimed, Inc., Maple Grove, MN (US)

( * ) Notice: Subject to any disclaimer, the term of this patent is extended or adjusted under 35 U.S.C. 154(b) by 1022 days.

(21) Appl. No.: 17/247,568

(22) Filed: Dec. 16, 2020

(65) Prior Publication Data

US 2021/0235969 A1 Aug. 5, 2021

Related U.S. Application Data

(60) Provisional application No. 62/969,353, filed on Feb. 3, 2020.

(51) Int. Cl.
*A61B 1/00* (2006.01)
*A61B 1/005* (2006.01)
(Continued)

(52) U.S. Cl.
CPC ........ *A61B 1/00087* (2013.01); *A61B 1/0008* (2013.01); *A61B 1/0014* (2013.01);
(Continued)

(58) Field of Classification Search
CPC .......... A61B 2017/00327; A61B 1/018; A61B 17/2909; A61B 18/1445;
(Continued)

(56) References Cited

U.S. PATENT DOCUMENTS

| | | |
|---|---|---|
| 4,942,866 A | 7/1990 | Usami |
| 5,762,069 A | 6/1998 | Kelleher et al. |
| 2011/0213363 A1 | 9/2011 | Cunningham et al. |
| 2013/0023923 A1 | 1/2013 | Mueller |
| 2021/0085386 A1* | 3/2021 | Rao ........................ A61B 5/287 |

FOREIGN PATENT DOCUMENTS

| | | |
|---|---|---|
| AU | 2016341269 | 5/2018 |
| EP | 1 620 164 | 5/2003 |

(Continued)

*Primary Examiner* — Tiffany Legette
(74) *Attorney, Agent, or Firm* — Fay Kaplun & Marcin, LLP

(57) ABSTRACT

A device includes a handle, a shaft and a steering mechanism. The handle includes a first actuator for an end effector. The shaft extends from the handle and sized and shaped to pass through a working channel of an endoscope. A distal end of the shaft includes the end effector. A pull wire extends from the handle to the end effector for actuating the end effector. The mechanism includes a second actuator for bending the distal end relative to a longitudinal axis of the shaft. The mechanism includes a first steering wheel having a first steering wire extending therefrom to the distal end of the shaft. Rotating the second actuator rotates the first steering wheel and tensions the first steering wire to bend the shaft, the pull wire for the end effector remaining actuatable when the distal end is bent.

19 Claims, 9 Drawing Sheets

(51) Int. Cl.
*A61B 1/018* (2006.01)
*A61B 17/128* (2006.01)
*A61M 25/01* (2006.01)
*A61B 17/00* (2006.01)

(52) U.S. Cl.
CPC .......... *A61B 1/0052* (2013.01); *A61B 1/0057* (2013.01); *A61B 1/018* (2013.01); *A61B 17/1285* (2013.01); *A61M 25/0147* (2013.01); *A61B 2017/0034* (2013.01); *A61B 2017/00367* (2013.01); *A61B 2017/00424* (2013.01)

(58) Field of Classification Search
CPC . A61B 2017/2929; A61B 2018/00916; A61M 25/0147; A61M 25/0136; A61M 25/0133; A61M 25/0105; A61M 25/0138; A61M 25/0141; A61M 25/0144
See application file for complete search history.

(56) References Cited

FOREIGN PATENT DOCUMENTS

| | | |
|---|---|---|
| EP | 2 403 421 | 3/2009 |
| EP | 2823776 | 1/2015 |
| JP | S61170447 A | 8/1986 |
| JP | H0751272 A | 2/1995 |
| JP | H0833639 A | 2/1996 |
| JP | H0847498 A | 2/1996 |
| JP | H09528 A | 1/1997 |
| JP | 2005046488 A | 2/2005 |
| JP | 2006116194 A | 5/2006 |
| JP | 2008541797 A | 11/2008 |
| JP | 2009-539472 A | 11/2009 |
| JP | 2010505521 A | 2/2010 |
| WO | 2004/098701 | 11/2004 |
| WO | 2010/104755 | 9/2010 |

* cited by examiner

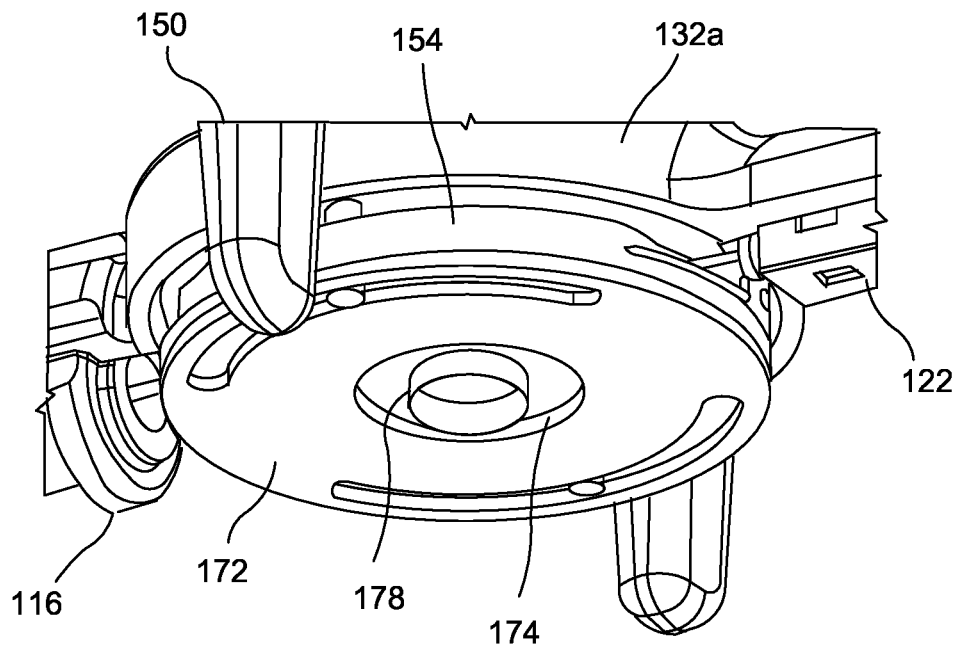
F I G. 14
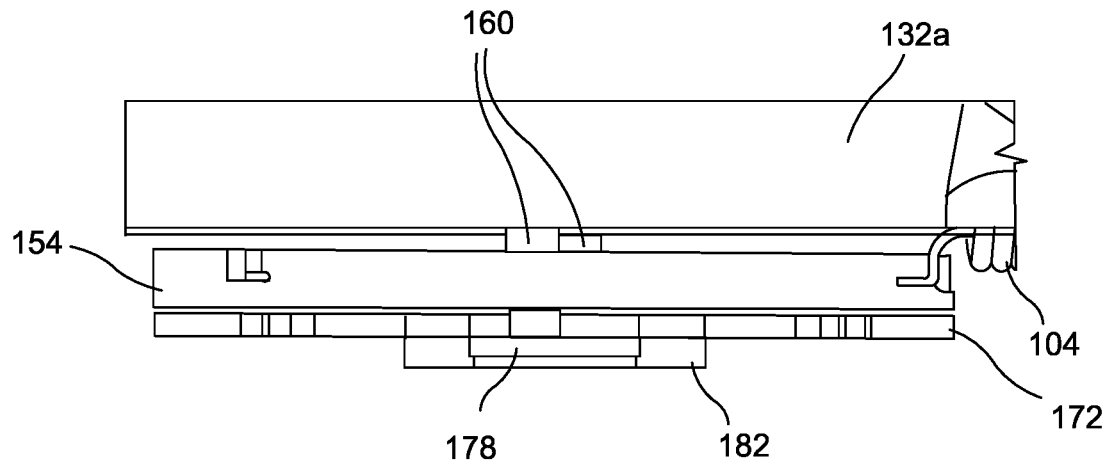
F I G. 15

STEERABLE ROTATIONAL HEMOSTASIS CLIP

PRIORITY INFORMATION

The disclosure claims priority to U.S. Provisional Patent Application Ser. No. 62/969,353 filed Feb. 3, 2020; the disclosure of which is incorporated herewith by reference.

FIELD

The present disclosure relates to hemostasis clips, in particular, a hemostasis clipping device with a rotatable and steerable distal end.

BACKGROUND

During endoscopic gastrointestinal (GI) procedures, the patient may be at risk of perforation of a wall of the GI tract or may require closure of the GI tract wall as part of the procedure. Hemostasis clips may be used for hemostasis of, for example, mucosal/sub-mucosal defects, bleeding ulcers, arteries, polyps, or diverticula, along with closure of luminal tract perforations. Some patient anatomy, such as the duodenum, is difficult to treat using front-viewing scopes because of its narrowness, and some hemostasis clipping systems are incompatible with side-viewing scopes, including duodenoscopes.

SUMMARY

The present disclosure relates to a device which includes a handle, a shaft and a steering mechanism. The handle includes a first actuator for an end effector. The shaft extends from the handle and sized and shaped to pass through a working channel of an endoscope. A distal end of the shaft includes the end effector. A pull wire extends from the handle to the end effector for actuating the end effector. The mechanism includes a second actuator for bending the distal end relative to a longitudinal axis of the shaft. The mechanism includes a first steering wheel having a first steering wire extending therefrom to the distal end of the shaft. Rotating the second actuator rotates the first steering wheel and tensions the first steering wire to bend the shaft, the pull wire for the end effector remaining actuatable when the distal end is bent.

In an embodiment, the first actuator couples to the pull wire to move the pull wire proximally and distally relative to the longitudinal axis of the shaft. Moving the pull wire actuates the end effector to move between a first configuration and a second configuration.

In an embodiment, the first actuator is a slidable spool.

In an embodiment, the end effector is a clip.

In an embodiment, the steering mechanism further includes a steering stopper fixed to a bottom surface of the first steering wheel limiting tension on the first steering wire.

In an embodiment, the steering mechanism further includes a locking mechanism for holding the end effector in a desired position.

In an embodiment, the locking mechanism further includes a locking knob; a threaded shaft extending from the locking knob toward the first steering wheel; and an annular brake plate at an end of the threaded shaft that joins to the first steering wheel.

In an embodiment, the device further includes a rotation knob rigidly fixed to the shaft. The rotation knob and the shaft rotate together about the longitudinal axis of the shaft.

In an embodiment, the rotation knob further includes a first rotation knob half; and a second rotation knob half. Each of the first and second rotation knob halves has a first recess at a proximal end and a second recess at a distal end, wherein the first recess is sized and shaped to receive a distal end of the handle and the second recess is sized and shaped to receive a proximal end of the shaft.

In an embodiment, the steering mechanism further includes a second steering wheel having a second steering wire extending therefrom to the distal end of the shaft. Rotating the second actuator rotates the second steering wheel and tensions the second steering wire to bend the shaft, the pull wire for the end effector remaining actuatable when the distal end is bent.

In an embodiment, actuating the first steering wheel bends the shaft in a first direction and actuating the second steering wheel bends the shaft in a second direction, the second direction opposite the first direction.

In an embodiment, the device further a locking knob; a threaded shaft extending from the locking knob toward the second steering wheel; and an annular brake plate at an end of the threaded shaft that joins the second steering wheel.

In an embodiment, the annular brake plate fits tightly onto a wheel ring protruding from a first surface of the second steering wheel.

In an embodiment, the device further includes a steering stopper fixed to a first surface of the second steering wheel limiting tension on the second steering wire. The present disclosure also relates to a device which includes a handle including a first actuator for a clip; a shaft extending from the handle, a distal end of the shaft including the clip, a pull wire extending from the handle to the clip for actuating the clip; a steering mechanism comprising a second actuator for bending the distal end relative to a longitudinal axis of the shaft, the steering mechanism comprising a steering wheel having a steering wire extending therefrom to the distal end of the shaft. Rotating the second actuator rotates the steering wheel and tensions the steering wire to bend the shaft, the pull wire for the clip remaining actuatable when the distal end is bent. In addition, the present disclosure relates to a method which includes inserting a shaft extending from a handle of a device through a working channel of an endoscope, the device including a first actuator for an end effector at a distal end of the shaft; drawing proximally a pull wire extending from the handle to the end effector by operating a first steering wheel of a steering mechanism to bend the distal end relative to a longitudinal axis of the shaft, the first steering wheel being coupled to a first steering wire extending therefrom to the distal end of the shaft; and actuating the pull wire to actuate the end effector.

In an embodiment, the end effector is actuated by sliding the first actuator proximally to move the end effector into a first configuration and sliding the first actuator distally to move the end effector into a second configuration.

In an embodiment, the method further includes rotating a rotation knob coupled to the shaft in a first direction to rotate the shaft in the first direction; and rotating the rotation knob in a second direction to rotate the shaft in the second direction opposite the first direction.

In an embodiment, the method further includes actuating a locking knob coupled to the steering mechanism to rotate a threaded shaft extending from the locking knob toward the first steering wheel in a first direction to position a brake plate at an end of the threaded shaft in contact with the first steering wheel to lock the distal end of the shaft in a desired configuration. In an embodiment, the method further includes rotating the locking knob in a second direction opposite the first direction to move the brake plate out of contact with the first steering wheel to permit rotation of the steering mechanism.

BRIEF DESCRIPTION

FIG. 14 shows a bottom perspective view of the lower steering wheel of the clipping device of FIG. 1.

FIG. 15 shows a semi-transparent side view of the lower steering wheel of the clipping device of FIG. 1.

DETAILED DESCRIPTION

Figure 1:
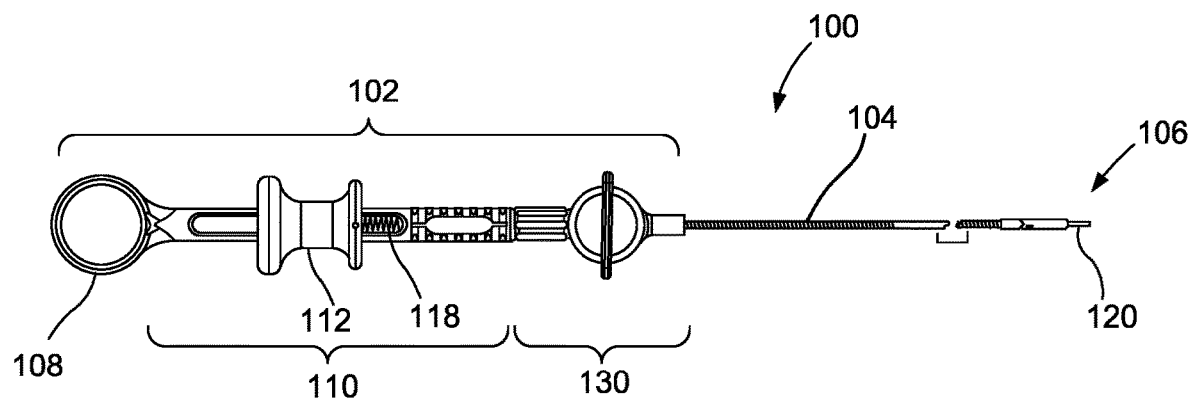
FIG. 1 shows a clipping device having rotation and steering mechanisms for controlling an orientation of a distal end.

The present disclosure may be further understood with reference to the following description and the appended drawings, wherein like elements are referred to with the same reference numerals. The present disclosure relates to a clipping device with a rotatable and steerable distal end for deploying a clip. The distal end is bendable to a sufficient degree to bring the clip within the field of view of a side-viewing endoscope. Additionally, full 360 deg rotatability provides access to difficult anatomies. A device handle includes a steering and rotation mechanism actuator (RSM) with a rotation knob and a steering knob, the handle further including an actuator for controlling a movement of the arms of the clip. Although the exemplary embodiments describe a hemostasis clipping device, the principles of the present disclosure may apply to other pull wire-actuated end effector devices, as will be described in detail below. The steerability of the clip allows the clips to be used with duodenoscopes and side viewing scopes. In addition, even when used in conjunction with a front viewing endoscope, these clips may be manipulable to reach tissue that is out of reach of other clips or that is more easily reached through the steering of the clip than through manipulation of the scope.

FIG. 1 shows a clipping device 100 including rotation and steering mechanisms enabling a user to control the orientation of a distal end 106 of the device 100 in multiple (e.g., six) degrees of freedom after it has been extended from an insertion device such as an endoscope. A handle 102 comprises actuators including, for example, a rotation knob 132, a steering knob 150, and a slidable spool 112 for deploying a clip 120. A flexible coiled shaft 104 extending distally from the handle 102 to the steerable distal end 106 defines a lumen therein housing steering and end effector pull wires. The distal end 106 in this embodiment is bendable through an effective angular range via the steering mechanism, as explained in detail below. In one embodiment the effective angular range is from 0 deg to 90 deg while in another embodiment, the effective angular range is from 0 deg to 70 deg.

Figure 4:
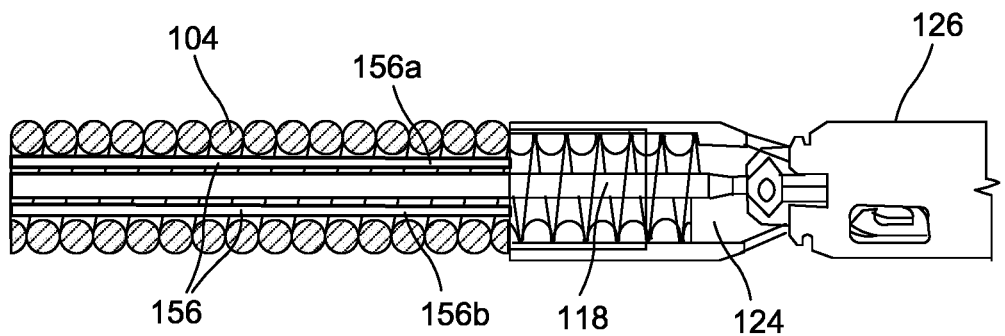
FIG. 4 shows the distal end of the coiled shaft of the clipping device of FIG. 1 coupling to a clip.
Figure 9:
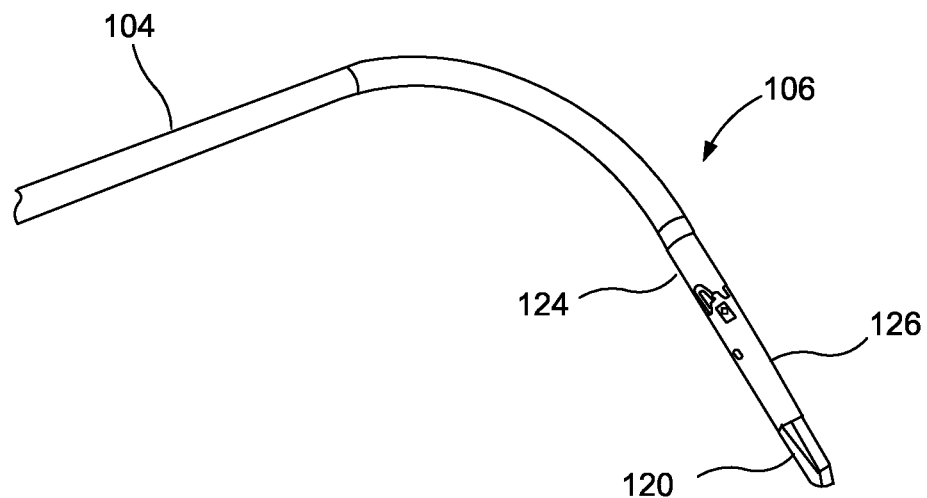
FIG. 9 shows the distal end of the clipping device of FIG. 1 in a bended state.
Figure 10:
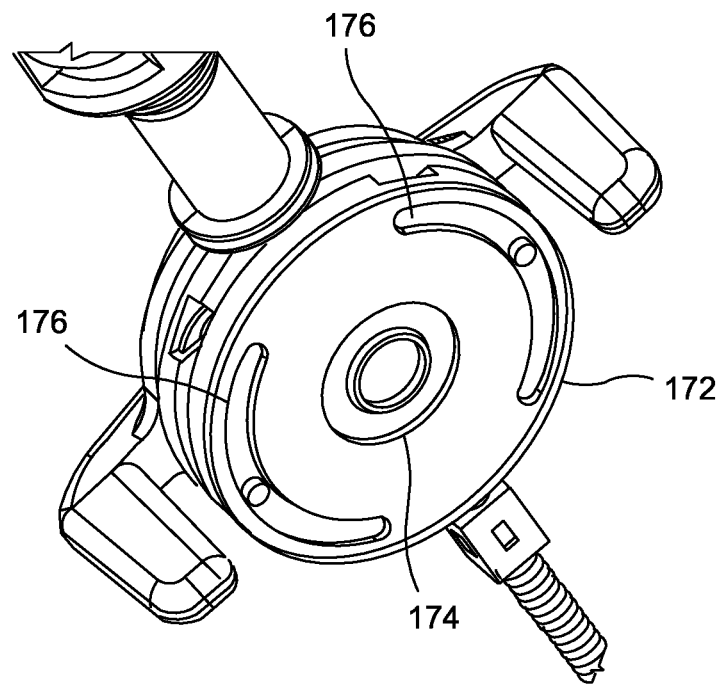
FIG. 10 shows the steering stopper of the clipping device of FIG. 1 engaged with the upper steering wheel.

The handle 102 includes a proximal thumb ring 108 configured to enable a user to insert a thumb therein to grip the handle 102. A handle shaft 110 extends distally from the thumb ring 108 and passes through the slidable spool 112 to couple to a proximal end of the coiled shaft 104. The slidable spool 112 serves, in this embodiment, as an actuator for the clipping mechanism. The slidable spool 112 is coupled to a proximal end of a pull wire 118 that extends distally through a channel in the handle 102 and continues through the lumen of the coiled shaft 104. The pull wire 118 extends distally through a coupling 124 (e.g., a bushing) attached to the proximal end of a capsule 126 housing the clip 120 to couple to the clip 120, as shown in FIGS. 4 and 9. Thus, motion of the spool 112 relative to the handle shaft 110 moves the pull wire 118 proximally and distally through the coiled shaft 104 to actuate the clip 120 as described below. U.S. patent application Ser. No. 15/589,620 describes an exemplary clipping device including a bushing, capsule and clip for use in an endoscopic procedure and is incorporated herein by reference.

The pull wire 118 is coupled, directly or indirectly, to the clip 120 so that sliding the spool 112 proximally along the longitudinal axis of the handle 102 from an initial distal position draws the pull wire 118 proximally, pulling the clip 120 into the capsule 126 so that contact between the wall of the capsule and the arms of the clip 120 draws the arms together to a closed, tissue gripping configuration. However, other pull wire-actuated mechanisms may be used to close the arms of the clip 120 without departing from the scope of the present disclosure. The spool 112, in this embodiment, is slidable in a longitudinal slot in the handle shaft 110.

Movement of the spool 112 distally along the handle shaft 110 moves the pull wire 118 distally pushing the clip 120 distally out of the capsule 126. In this embodiment, the arms of the clip 120 are biased toward an open, tissue receiving configuration so that, as the arms of the clip 120 are extended distally from the capsule 126, the clip arms, no longer constrained by the capsule 126 to the closed, tissue gripping configuration, spread apart from one another to the open, tissue receiving configuration. As would be understood by those skilled in the art, other clip actuators may be used without departing from the scope of the present disclosure. Further, as mentioned above, other pull wire-actuated end effectors may be used with the rotation and steering mechanisms described below. For example, the end effector may be scissors, a ligation band deployment, etc.

Figure 2:
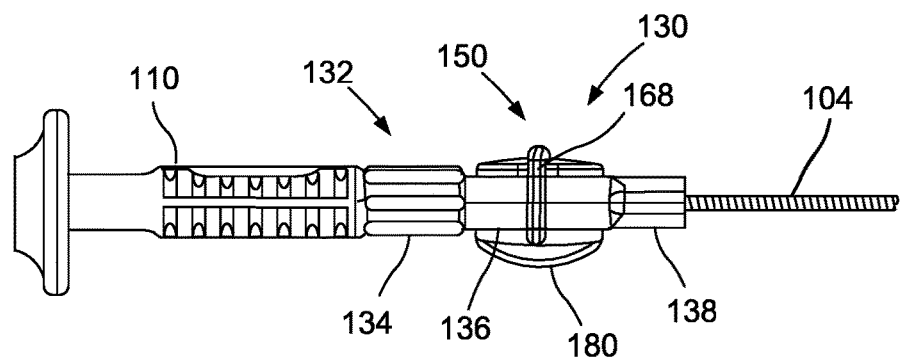
FIG. 2 shows a side view of the clipping device of FIG. 1.
Figure 3:
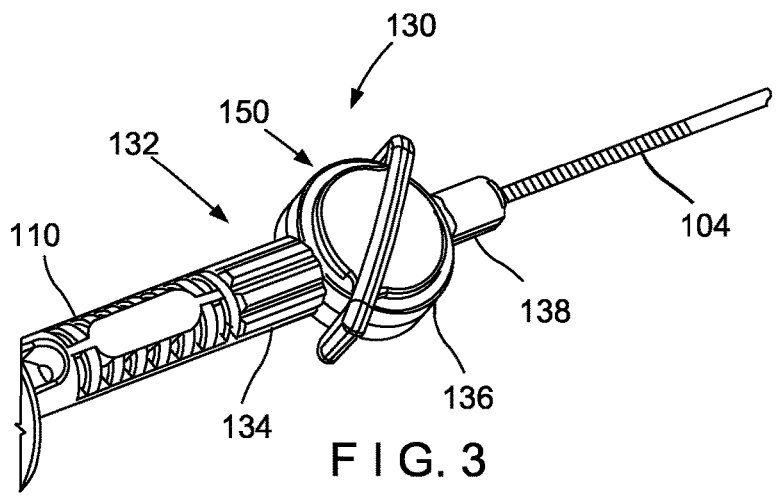
FIG. 3 shows a perspective view of the clipping device of FIG. 1.
Figure 5:
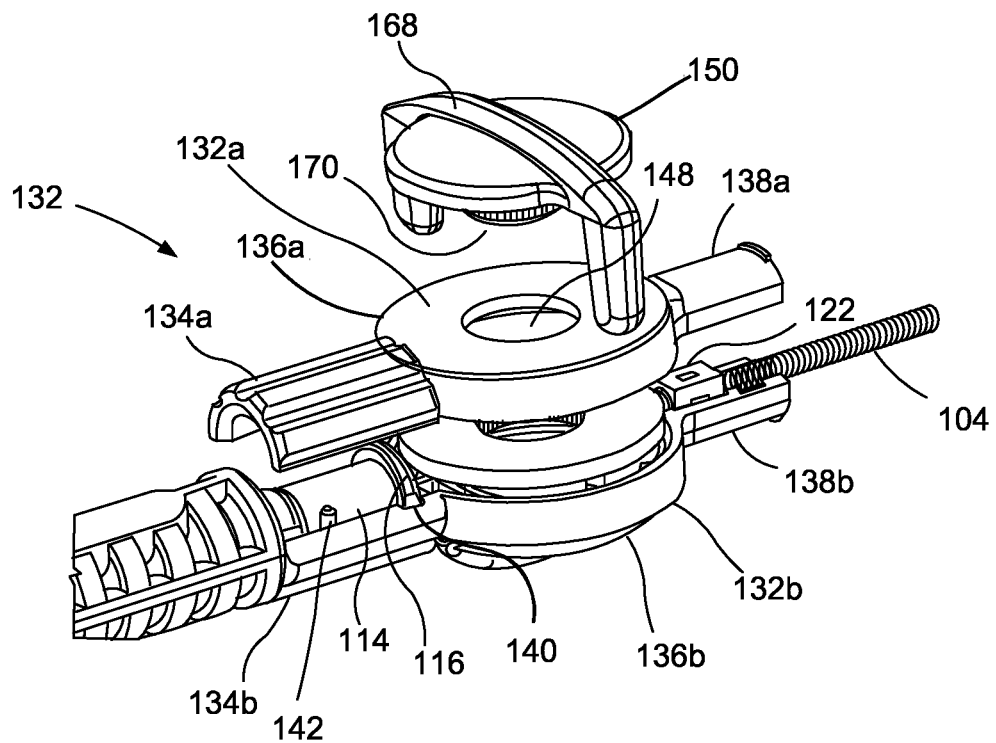
FIG. 5 shows an exploded view of the rotation knob of the clipping device of FIG. 1.

The rotation and steering mechanism actuator (RSM) 130 extends from the distal end of the handle shaft 110 and comprises a rotation knob 132 and a steering knob 150, as shown in FIGS. 2-3. The rotation knob 132 is composed of a first (upper) half 132a and a second (lower) half 132b joined to one another, a proximal portion 134 of the rotation knob 132 being joined over a distal end 114 of the handle shaft 110 to couple the rotation knob 132 thereto, as shown in FIG. 5, to be described further below. The assembled rotation knob 132 has the proximal portion 134, which may be gripped by a user and rotated about a longitudinal axis of the handle 102, a distal portion 138 that couples the rotation knob 132 to the coiled shaft 104 via a crimped square 122 (to be described below), such that the shaft 104 rotates together with the rotation knob 132, and a middle portion 136 joining the proximal and distal portions 134, 138 and providing a space to accommodate further device components, to be described below.

In the present embodiment, each of the halves of the proximal portion 134a, 134b has a semi-circular cross-section relative to a transverse plane of the handle 102 and the halves 134a and 134b are clipped to one another over the distal end 114 of the handle shaft 110. The distal end 114 of the handle shaft 110 is cylindrical with a cylindrical ridge 116 at its distal tip, the ridge 116 having an increased diameter relative to the remainder of the distal end 114. A recess 140 is formed from recess halves 140a, 140b on the inner surface of each of the proximal portion 134a, 134b of the rotation knob 132a, 132b near a distal end of each of the rotation knob 132a, 132b. The recess 140 is sized and shaped to receive therein the cylindrical ridge 116 of the distal end 114 of the handle shaft 110. Each of the proximal portion halves 134a, 134b has a pin 142 extending toward the other of the halves 134a, 134b.

Figure 13A:
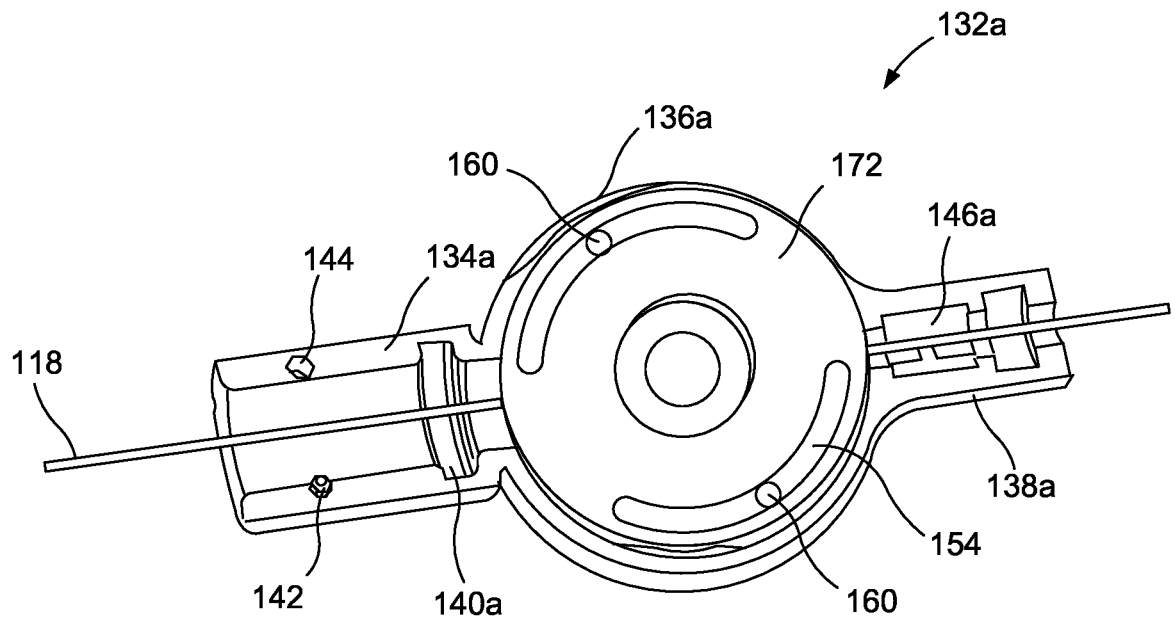
FIG. 13a shows an interior view of an upper rotation knob half of FIG. 5.
Figure 13B:
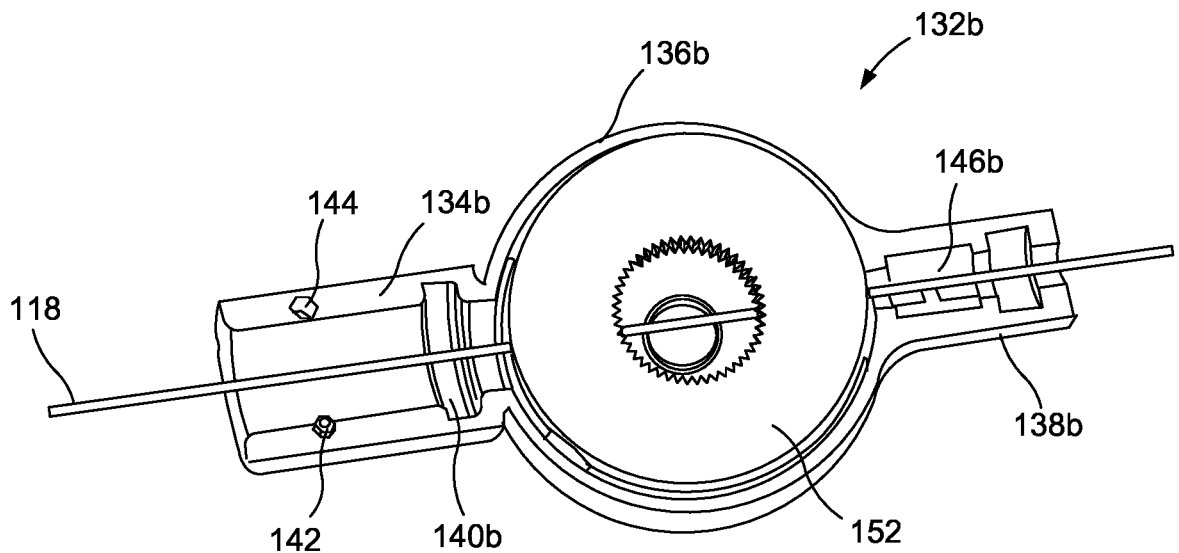
FIG. 13b shows an interior view of a lower rotation knob half of FIG. 5.
Figure 16:
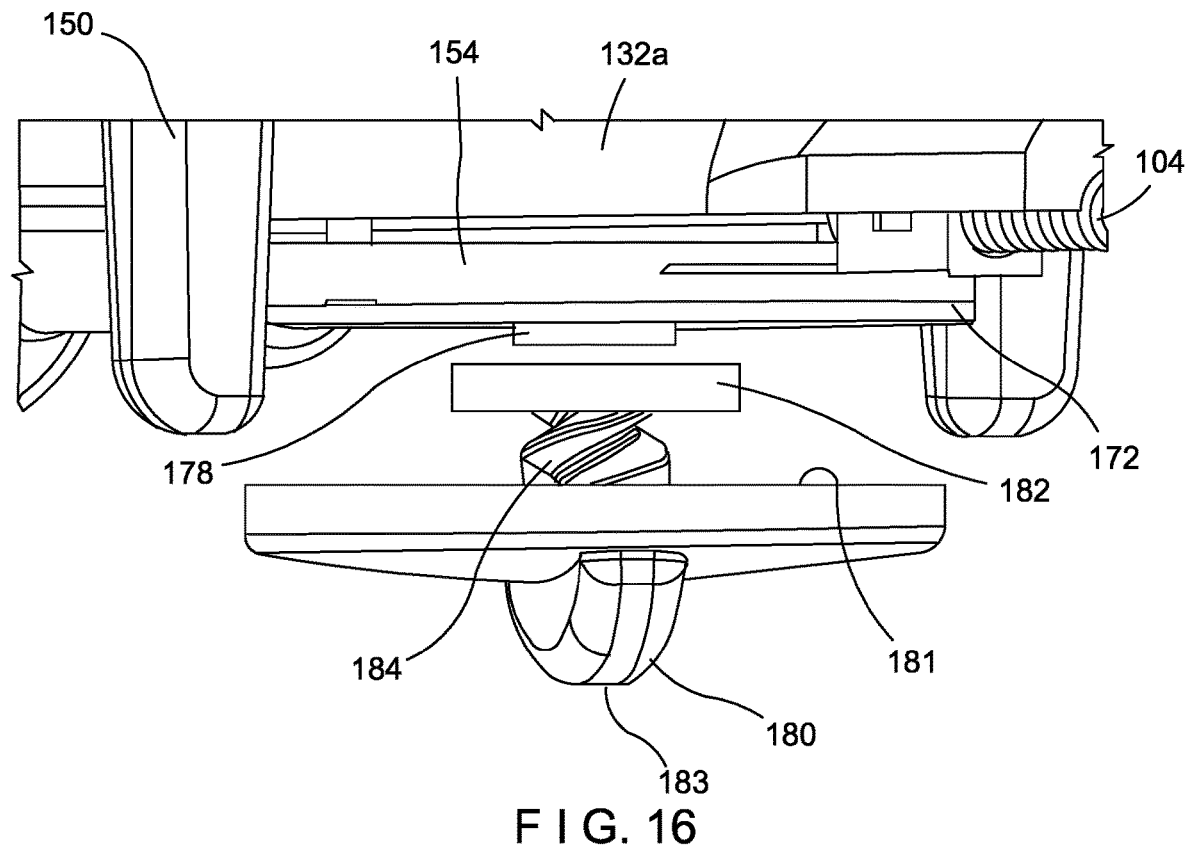
FIG. 16 shows a side view of the lower steering wheel with the annular brake plate and the locking knob of the device of FIG. 1.
Figure 17:
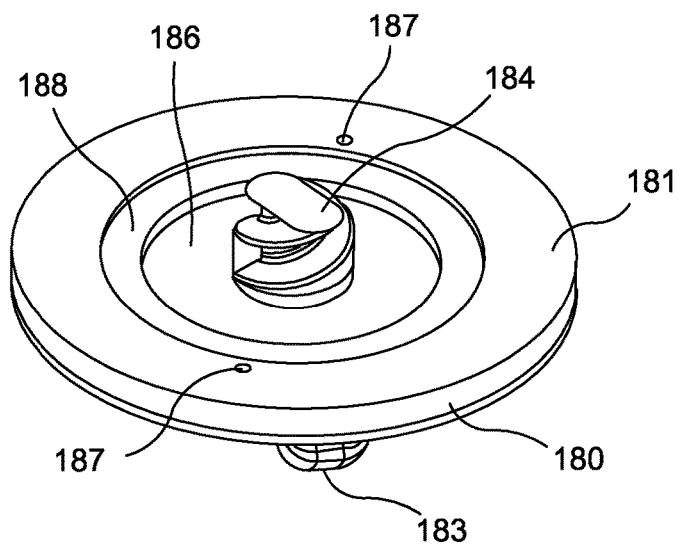
FIG. 17 shows a perspective top view of the locking knob of FIG. 16.

As the rotation knob halves 132a, 132b are joined to one another, each pin 142 is inserted into a corresponding pin hole 144 so that the rotation knob halves 132a, 132b snap together, as shown in FIGS. 13a-13b. When the proximal portion halves 134a, 134b are snapped together around the distal end 114 of the handle shaft 110, the distal ridge 116 inserts into the recess 140 and fixes the rotation knob 132 longitudinally relative to the handle 102, while allowing the rotation knob 132 to rotate about the longitudinal axis of the handle 102. Although FIGS. 13a-13b show one pin 142 and one pin hole 144 on each of rotation knob halves 132a, 132b, one with ordinary skill in the art will understand that each of the rotation knob halves 132a, 132b, may have a greater number of pins 142 and correspondingly, a greater number of pin holes 144.

In this embodiment, each of the distal portion halves 138a, 138b of the rotation knob 132 has a substantially cylindrical outer surface, although any outer shape may be used. The inner surface of each of the distal portion halves 138a, 138b has a recess 146a, 146b with a rectangular cross section sized and shaped to receive the square 122, the square 122 being crimped toward the proximal end of the coiled shaft 104. When the rotation knob halves 132a, 132b are joined, the crimped square 122 is held in a fixed position relative to the rotation knob 132 so that rotation of the rotation knob 132 rotates the coiled shaft 104 in conjunction therewith. Thus, it may be seen that the RSM 130 and the coiled shaft 104 have full 360 deg rotatability relative to the handle shaft 110.

In summary, the RSM 130 is coupled to the handle shaft 110 via the cylindrical distal ridge 116 of the handle shaft 110 which is received in the cylindrical recess 140 in the proximal portion 134 of the rotation knob 132, allowing for free rotation of the RSM 130 relative to the handle shaft 110, while the coiled shaft 104 is rotationally fixed relative to the RSM 130 via the crimped square 122 received in the rectangular recess 146 in the distal portion 138 of the rotation knob 132. Thus, the coiled shaft 104 and the distal end 106 of the device 100, including the clip 120, may be freely rotated together, in unison with the rotation knob 132. When the distal end 106 is additionally steered, as described below, the rotatability of the distal end 106 facilitates access to difficult-to-reach anatomies to be clipped or otherwise treated that would be difficult or impossible to reach with non-steerable scopes as would be understood by those skilled in the art.

The middle portion 136 of the rotation knob 132 functions in part as a support structure for the steering knob 150, elements of which are found interior to and exterior to the middle portion 136. Each middle portion half 136a, 136b has a hollow cylindrical shape with a hole 148 extending through its exterior side and an open interior side, so that, when joined, the middle portion 136 is a substantially hollow cylinder with a hole 148 extending through its top and bottom sides.

Figure 6:
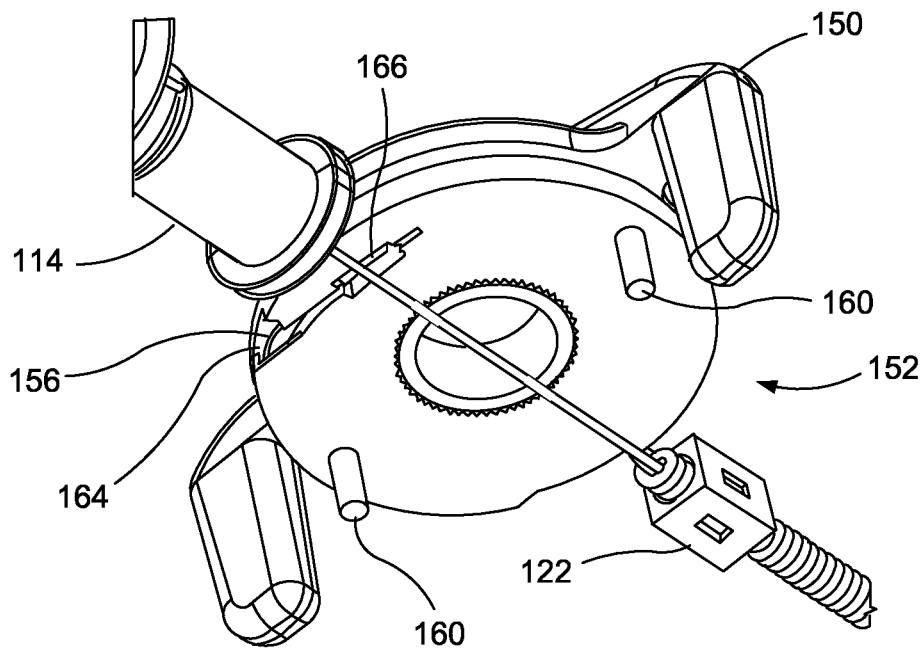
FIG. 6 shows a bottom perspective view of the upper steering wheel of the clipping device of FIG. 1.
Figure 7:
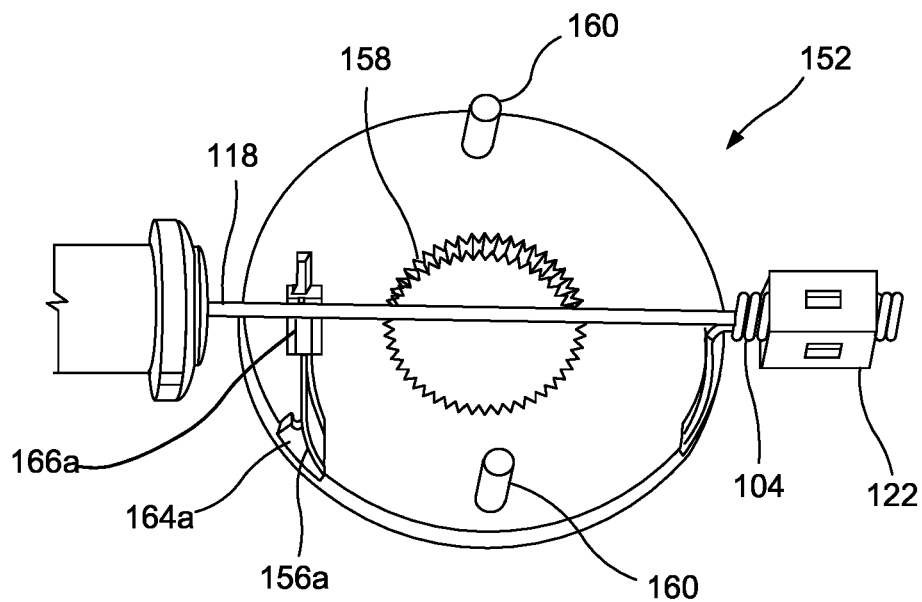
FIG. 7 shows a bottom view of the upper steering wheel of the clipping device of FIG. 1.
Figure 8:
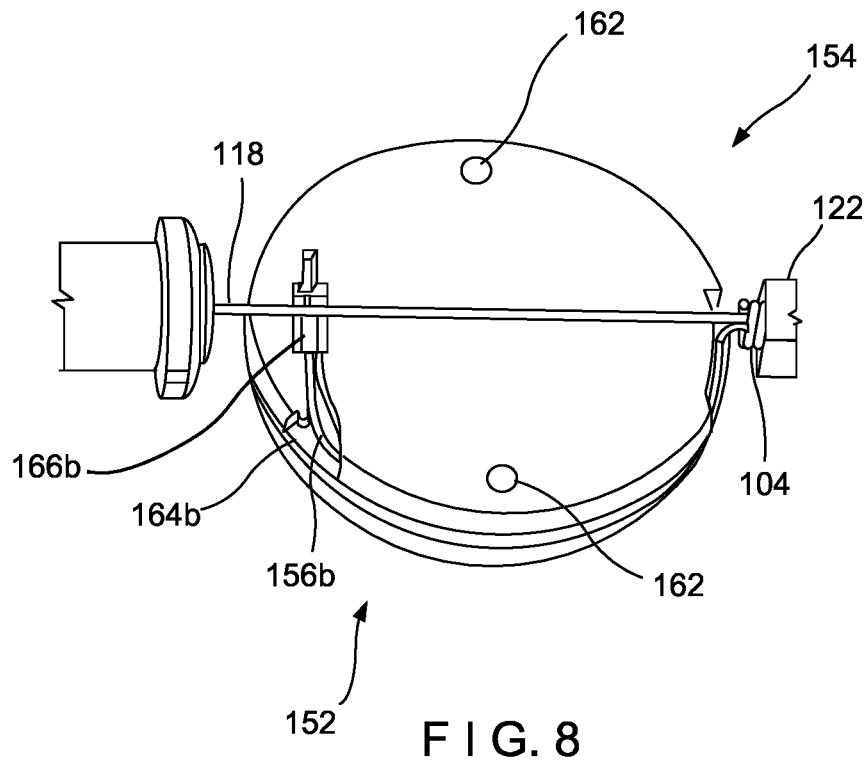
FIG. 8 shows a top view of the lower steering wheel of the clipping device of FIG. 1.

In this embodiment, the steering mechanism includes an upper steering wheel 152, as shown in FIGS. 6-7, and a lower steering wheel 154, as shown in FIG. 8, each steering wheel being coupled to a respective steering pull wire 156a, 156b extending from the RSM 130 through the coiled shaft 104 to the proximal end of the coupling 124 that connects the coiled shaft 104 to the clip 120, as shown in FIG. 4. When one of the steering wires 156a, 156b is tensioned via the steering knob 150 the coiled shaft 104 bends to the direction of the tensioned wire so that the distal end 106 of the device 100 is directed away from the longitudinal axis of the device 100, as shown, for example, in FIG. 9. The wires 156a, 156b are adhered to and extend along opposing sides of the coiled shaft 104, allowing for bending in either of two opposing directions.

However, another embodiment may include only a single steering wire inducing bending in a single direction as, when combined with the steering capability the device may still be oriented and directed in any desired orientation/direction. As seen in FIG. 4, the pull wire 118 for the clip 120 is independent of the steering pull wires 156a, 156b and may move independently thereof. To be described in detail below, the steering mechanism includes a steering stopper 172 fixed to the lower steering wheel 154 that limits the degree of tension that may be applied to either of the steering wires 156a, 156b. The steering mechanism further includes a locking knob 180 that allows the physician to hold the tension of the wires, and consequently the bend of the distal end 106, at a fixed degree.

The upper steering wheel 152 is annular, having a thin disc-shaped body with a hole extending through its middle, an inner surface 158 of the annulus having a geared profile mated to a geared section 170 of the steering knob 150, as described further below. The lower steering wheel 154 of this embodiment is similarly disc-shaped, but does not have a through hole. The upper steering wheel 152 is arranged in the hollow interior of the upper half 136a of the middle portion 136 of the rotation knob 132, while the lower steering wheel 154 is arranged in the hollow interior of the lower half 136b of the middle portion 136 of the rotation knob 132.

Two pins 160 extending from a lower surface of the upper steering wheel 152 are sized to be inserted into corresponding pin holes 162 in the lower steering wheel 154 to attach the steering wheels 152, 154. The pin holes 162 extend through the lower steering wheel 154 and, when the pins 160 are inserted fully therein, the pins 160 extend past the lower surface of the lower steering wheel 154 to engage the steering stopper 172. Each of the steering wheels 152, 154 has an interior channel 164 through which a steering wire 156 extends from an attachment crimp 166. The channels 164 extend about a portion of the wheels 152, 154 near the outer diameters of the discs.

Specifically, as seen in FIGS. 7-8, the upper steering wheel 152 has an interior channel 164a originating at a first side of the wheel 152 and extending through a substantially circular path near the outer diameter of the wheel 152 to a second, opposing side of the wheel 152. When the upper steering wheel 152 is in an unactuated position the first side of the wheel 152 is a proximal side and the second side of the wheel 152 is a distal side. However, these relative orientations of proximal and distal will change as the wheel 152 is rotated. The interior channel 164a is open on the first side so that the steering wire 156a may be attached to the wheel 152 via the crimp 166a.

The interior channel 164a is similarly open on the second side so that the steering wire 156a may extend out of the channel 164a and into the coiled shaft 104. The remainder of the channel 164a is closed to constrain the steering wire 156a on the channel path during a tensioning or slacking of the wire 156a, to be explained below. The lower steering wheel 154, similar to the upper steering wheel 152, has an interior channel 164b originating at a first side of the wheel 154 and extending through a substantially circular path near the outer diameter of the wheel 154 to a second, opposing side of the wheel 154. However, when the wheels 152, 154 are joined via the pins 160 and pin holes 162, the circular paths of the wheel channels 164a, 164b extend in opposing directions. For example, if the upper steering wheel 152 has a channel 164a extending clockwise relative to a top view of the assembled, unactuated RSM 130, the lower steering wheel has a channel 164b extending counterclockwise relative to the top view.

When the lower steering wheel 154 is in an unactuated position the first side of the wheel 154 is a proximal side and the second side of the wheel 154 is a distal side. Similar to the upper steering wheel 152, the relative orientations of proximal and distal for the lower steering wheel 154 will change as the wheel is rotated. The lower steering wheel 154 is open on the first side so that the steering wire 156b may be attached to the wheel 154 via the crimp 166b. The interior channel 164b is similarly open on the second side so that steering wire 156b may extend out of the channel 164b and into the coiled shaft 104. The remainder of the channel 164b is closed to constrain the steering wire 156b on the channel path during a tensioning or slacking of the wire 156b.

Considering the rigid attachment between the upper and lower steering wheels 154, 156 and the opposing paths for the steering wire channels 164a, 164b, it may be seen that rotation of the wheels 152, 154 will tension one of the wires 156 while slacking the other of the wires 156. Specifically, considering the aforementioned example where the upper steering wire 156a extends clockwise from a proximal attachment point to a distal point, where it then extends through the coiled shaft 104, it may be seen that counterclockwise rotation of the upper steering wheel 152 will tension the wire 156a by rotating the attachment point for the wire 156a, i.e., the crimp 166a, away from the path of the wire 156a, thus drawing the wire 156a proximally out of the coiled shaft 104. Conversely, the lower steering wire 156b extends counterclockwise from the proximal attachment point to the distal point, where it then extends through the coiled shaft 104, and will slack when the lower steering wheel 154 is rotated counterclockwise by rotating the attachment point for the wire 156b, i.e., the crimp 166b, toward the path of the wire 156b, thus pushing the wire 156b further distally into the coiled shaft 104.

The opposed tensioning/slacking for the two steering wires 156 causes the distal end 106 of the device 100 to bend in the direction of the tensioned steering wire 156 while the slacked steering wire 156 is slacked enough to allow the bending. Each of the steering wires 156 may be welded to the distal end 106 to control the bending of the distal end 106. In another embodiment, the steering wire 156 may extend through a sheath, the sheath may then be attached (e.g., welded) to the coiled shaft 104. The degree of rotation of the upper and lower steering wheels 154, 156 directly correlates to the degree of bending of the distal end 106. Thus, a physician actuating the steering wheels 154, 156 by turning the steering knob 150 has precise control over the bending of the distal end 106 and, consequently, the position of the clip 120.

The steering knob 150 has a ridged handle portion 168 extending transversely across the disc-shaped body of the steering knob 150, the handle portion 168 further having ends overhanging the sides of the disc-shaped body. The ridge or either of the sides of the handle portion 168 may be gripped by the physician to rotate the steering knob 150. The steering knob 150 is coupled to the upper steering wheel 152 via a geared section 170 sized and shaped to fit into the geared inner surface 158 of the upper steering wheel 152. The steering knob 150, with the exception of the geared section 170, remains external to the rotation knob 132, with the geared section 170 extending through the hole 148 in the middle portion of the upper rotation knob half 132a to engage the upper steering wheel 152. The additional mating of the upper steering wheel 152 to the lower steering wheel 154 via the pins 160 and the pin holes 162 allows the physician to effectively rotate both wheels 152, 154 via the steering knob 150 in a synchronized manner.

The extent of the rotation of the steering wheels 152, 154 is limited by a steering stopper 172 fixed to the lower rotation knob 132b. The steering stopper 172 may be fixed to the lower rotation knob 132b via a fixation mechanism (e.g., a snap fit, a pin/hole mating, etc.), the fixation mechanism preventing the steering stopper 172 from rotating relative to the lower rotation knob 132b. The steering stopper 172 is annular, having an outer diameter substantially similar to the diameters of the steering wheels 152, 154 and a includes through hole 174 extending therethrough. The steering stopper 172 further has two pin channels 176 sized to receive the pins 160 extending off the upper steering wheel 152 and through the pin holes 162 in the lower steering wheel 154.

Each of the pin channels 176 extends about a portion of an arc of a circle, e.g., ~90 deg of a full circle, such that the pins 160 of the upper steering wheel 152 are constrained from further rotation by the ends of the channels 176 as the steering wheels 152, 154 are rotated. When the steering knob 150 is in an unactuated state, i.e., when neither of the steering wires 156 is tensioned, the pins 160 are located at or near the center of the pin channels 176. Rotation of the steering knob 150 by ~45 deg in either direction will bring both of the pins 160 into contact with one of the ends of the channels 176, thus delimiting the range of motion of the steering wheels 152, 154 and the extent of the bending of the distal end 106 of the device 100.

As shown in FIGS. 14-17, the RSM 130 additionally has a locking mechanism to hold the bending of the distal end 106 in a desired position. The locking mechanism includes an annular brake plate 182 that, when rotated via a locking knob 180, joins the lower steering wheel 154 to the fixed steering stopper 172, preventing the steering wheels 152, 154 from rotating. The brake plate 182 fits tightly into the hole 174 of the steering stopper 172. Accordingly, the brake plate 182 mates tightly with a wheel ring 178 of the lower steering wheel 154, restraining movement of the lower steering wheel 154 from a resulting friction force between the brake plate 182 and the wheel ring 178. The wheel ring 178 has an interior threaded portion which corresponds to a threaded shaft 184 of the locking knob 180. The threaded shaft 184 extends from a center of the locking knob 180 toward the wheel ring 178. The threaded shaft 184 is rotationally fixed relative to the locking knob 180, in other words, the threaded shaft 184 is rotated with the locking knob 180 in a synchronized manner, to be described below.

The locking knob 180 extends from a first surface 181 to a second surface 183. Further, the locking knob 180 includes a first cavity 186 and a second cavity 188. The first cavity 186 is sized and shaped to receive therein the wheel ring 178 of the lower steering wheel 154. The second cavity 188 is sized and shaped to receive therein the brake plate 182. The first cavity 186 and the second cavity 188 extend radially from the center of the locking knob 180, the first cavity 186 having a diameter smaller than a diameter of the second cavity 188. The first cavity 186 and the second cavity 188 extend from the first surface 181 toward the second surface 183.

The first cavity 186 extends a further distance toward the second surface 183 relative to the second cavity 188. In other words, a bottom of the first cavity 186 is closer to the second surface 183 than a bottom of the second cavity 188. The locking knob 180 further includes holes 187 extending from the first surface 181 toward the second surface 183. The holes 187 are sized and shaped to receive therein the pins 160, the pins 160 extending from the upper steering wheel 152 through the lower steering wheel 154 and the steering stopper 172. The pins 160 stop in the holes 187 of the locking knob 180, thereby locking the pins 160 relative to the locking knob 180.

Rotating the locking knob 180 in a first direction, e.g. clockwise, translates the brake plate 182 upward to engage the lower steering wheel 154 with the steering stopper 172 which, as previously mentioned, is fixed to the rotation knob 132. Thus, the steering wheels 152, 154 are fixed at their current rotational orientations, locking the distal end 106 of the device 100 at the current degree of bending. Rotating the locking knob 180 in the reverse direction, e.g. counterclockwise, releases the brake plate 182, allowing free steerable rotation. If the physician is not engaging the steering knob 150 when the brake plate 182 is released, the distal end 106 will, absent forces applied by surrounding tissue, return to a substantially straight position, as there is no tension in the steering wires 156.

Figure 11:
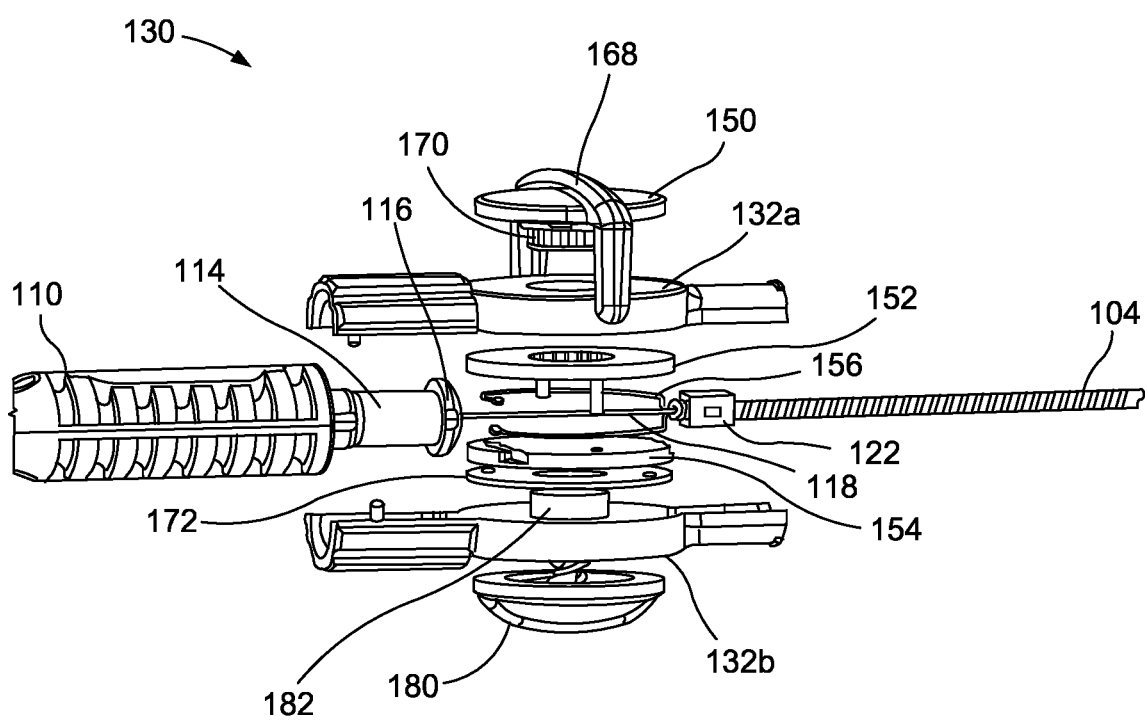
FIG. 11 shows an exploded view of the RSM of the clipping device of FIG. 1.
Figure 12:
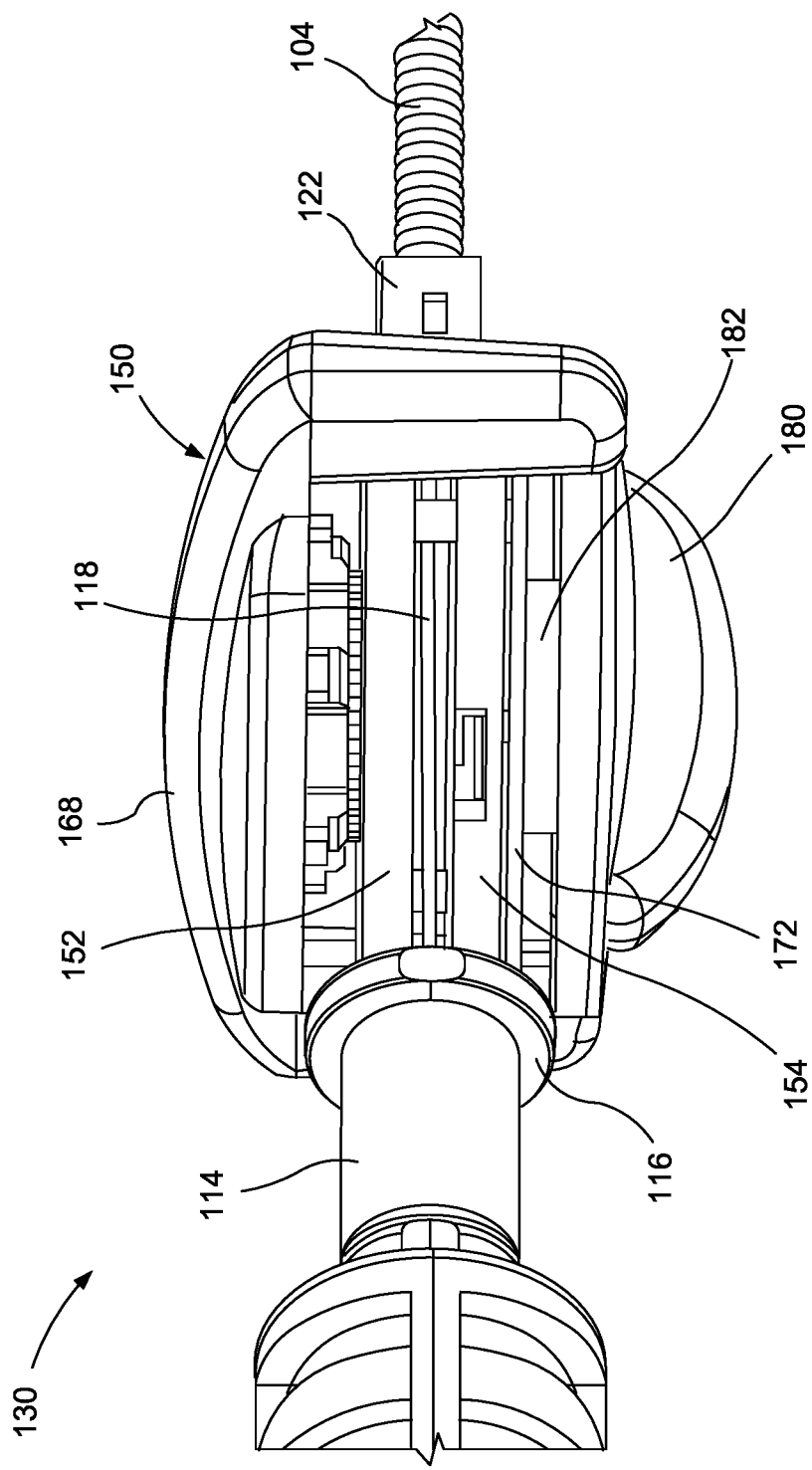
FIG. 12 shows the assembled RSM of the clipping device of FIG. 1, excluding the rotation knob.

FIG. 11 shows an exploded view of the RSM 130 of the clipping device 100, where the various layers of the RSM 130 are shown in a separated state, for clarity purposes. FIG. 12 shows the assembled RSM 130 excluding the rotation knob 132 so that the arrangement of the internal components may be seen.

It will be appreciated by those skilled in the art that changes may be made to the embodiments described above without departing from the inventive concept thereof. It should further be appreciated that structural features and methods associated with one of the embodiments can be incorporated into other embodiments. It is understood, therefore, that this invention is not limited to the particular embodiment disclosed, but rather modifications are also covered within the scope of the present invention as defined by the appended claims.

The invention claimed is:

1. A device, comprising:
    a handle including a first actuator for a hemostatic clip:
    a flexible coiled shaft extending from the handle, the flexible coiled shaft being sized and shaped to pass through a working channel of an endoscope, a distal end of the flexible coiled shaft including the hemostatic clip, a pull wire extending from the handle to the hemostatic clip for actuating the hemostatic clip; and
    a steering mechanism comprising a second actuator for bending the distal end relative to a longitudinal axis of the flexible coiled shaft, the steering mechanism comprising a first steering wheel having only a single first steering wire extending therefrom to the distal end of the flexible coiled shaft,
    wherein rotating the second actuator rotates the first steering wheel and tensions the first steering wire to bend the flexible coiled shaft, the pull wire for the hemostatic clip remaining actuatable when the distal end is bent.

2. The device of claim 1, wherein the steering mechanism further comprises:
    a steering stopper fixed to a bottom surface of the first steering wheel limiting tension on the first steering wire.

3. The device of claim 1, wherein the first actuator couples to the pull wire to move the pull wire proximally and distally relative to the longitudinal axis of the flexible coiled shaft, wherein moving the pull wire actuates the hemostatic clip to move the hemostatic clip between a first configuration and a second configuration.

4. The device of claim 3, wherein the first actuator is a slidable spool.

5. The device of claim 1, wherein the steering mechanism further comprises:
    a locking mechanism for holding the hemostatic clip in a desired position.

6. The device of claim 5, wherein the locking mechanism further comprises:
    a locking knob;
    a threaded shaft extending from the locking knob toward the first steering wheel; and
    an annular brake plate at an end of the threaded shaft that joins to the first steering wheel.

7. The device of claim 1, further comprising:
    a rotation knob rigidly fixed to the flexible coiled shaft,
    wherein the rotation knob and the flexible coiled shaft rotate together about the longitudinal axis of the flexible coiled shaft.

8. The device of claim 7, wherein the rotation knob further comprises:
    a first rotation knob half, and
    a second rotation knob half,
    wherein, each of the first and second rotation knob halves has a first recess at a proximal end and a second recess at a distal end, wherein the first recess is sized and shaped to receive a distal end of the handle and the second recess is sized and shaped to receive a proximal end of the flexible coiled shaft.

9. The device of claim 1, wherein the steering mechanism further comprises:
    a second steering wheel having only a single a second steering wire extending therefrom to the distal end of the flexible coiled shaft, wherein rotating the second actuator rotates the second steering wheel and tensions the second steering wire to bend the flexible coiled shaft, the pull wire for the hemostatic clip remaining actuatable when the distal end is bent.

10. The device of claim 9, wherein actuating the first steering wheel bends the flexible coiled shaft in a first direction and actuating the second steering wheel bends the flexible coiled shaft in a second direction, the second direction opposite the first direction.

11. The device of claim 9, further comprising:
a steering stopper fixed to a first surface of the second steering wheel limiting tension on the second steering wire.

12. The device of claim 9, further comprising:
a locking knob;
a threaded shaft extending from the locking knob toward the second steering wheel; and
an annular brake plate at an end of the threaded shaft that joins the second steering wheel.

13. The device of claim 12, wherein the annular brake plate fits tightly onto a wheel ring protruding from a first surface of the second steering wheel.

14. A device, comprising:
a handle including a first actuator for a clip;
a flexible coiled shaft extending from the handle, a distal end of the flexible coiled shaft including the clip, a pull wire extending from the handle to the clip for actuating the clip; and
a steering mechanism comprising a second actuator for bending the distal end relative to a longitudinal axis of the flexible coiled shaft, the steering mechanism comprising a steering wheel having a only a single steering wire extending therefrom to the distal end of the flexible coiled shaft,
wherein rotating the second actuator rotates the steering wheel and tensions the steering wire to bend the flexible coiled shaft, the pull wire for the clip remaining actuatable when the distal end is bent.

15. A method, comprising: inserting a flexible coiled shaft extending from a handle of a device through a working channel of an endoscope, the device including a first actuator for a hemostatic clip—at a distal end of the flexible coiled shaft; drawing proximally a pull wire extending from the handle to the hemostatic clip by operating a first steering wheel of a steering mechanism to bend the distal end relative to a longitudinal axis of the flexible coiled shaft, the first steering wheel being coupled to only a single first steering wire extending therefrom to the distal end of the flexible coiled shaft; and actuating the pull wire to actuate the hemostatic clip.

16. The method of claim 15, wherein the hemostatic clip is actuated by sliding the first actuator proximally to move the hemostatic clip into a first configuration and sliding the first actuator distally to move the hemostatic clip into a second configuration.

17. The method of claim 15, further comprising:
rotating a rotation knob coupled to the shaft in a first direction to rotate the flexible coiled shaft in the first direction; and
rotating the rotation knob in a second direction to rotate the flexible coiled shaft in the second direction opposite the first direction.

18. The method of claim 15, further comprising:
actuating a locking knob coupled to the steering mechanism to rotate a threaded shaft extending from the locking knob toward the first steering wheel in a first direction to position a brake plate at an end of the threaded shaft in contact with the first steering wheel to lock the distal end of the shaft in a desired configuration.

19. The method of claim 18, further comprising:
rotating the locking knob in a second direction opposite the first direction to move the brake plate out of contact with the first steering wheel to permit rotation of the steering mechanism.

* * * * *